Nov. 2, 1948. L. A. TUTTLE Plant Pat. 810
ROSE PLANT
Filed April 21, 1947
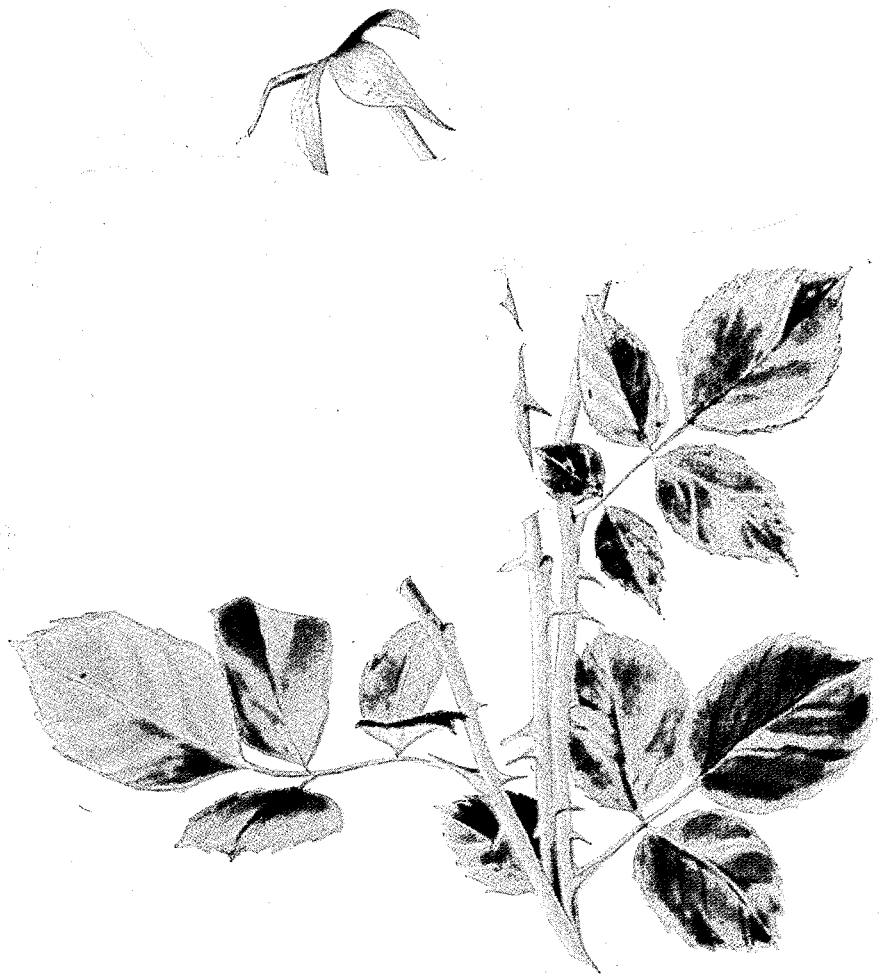
Inventor
Leslie A. Tuttle
Lyon & Lyon
By Attorneys Patented Nov. 2, 1948

Plant Pat. 810

UNITED STATES PATENT OFFICE

810

ROSE PLANT

Leslie A. Tuttle, Pasadena, Calif., assignor to Tuttle Bros. Nurseries, Pasadena, Calif., a partnership composed of Leslie A. Tuttle and Harry E. Tuttle Application April 21, 1947, Serial No. 742,881

1 Claim. (Cl. 47—61)

This invention relates to a new and distinctive variety of rose having the hereinafter set forth characteristics: The parentage of the rose bush forming the subject matter of this application is not exactly known other than that it was developed from a sport of the rose "Picture" which, to applicant's knowledge, is not a patented rose. The rose is fully illustrated in the accompanying color print showing the rose as a bud, in semi- and in full-bloom, together with the foliage and stock or stems supporting the rose.

The new and distinct variety of rose embodying this invention is characterized by the following:

The rose of this invention may be compared with the rose "Picture" in its form, shape of leaves, thorniness, habits of growth, profusion and periods of bloom. It has the same degree of susceptibility to insect infestation and fungus disease as its parent, the rose "Picture," but no more so.

The buds of the rose of this invention, and also the open blooms, are of the same size and shape as those of its parent, but the rose of this invention has fewer petals, there being generally 18 petals to the bloom.

The buds and flower of the parent rose "Picture" are velvety clear rose pink throughout. The buds and flowers of this rose have the following color characteristics: The colors hereafter specifically referred to are given by reference to the Horticultural Color Chart issued by The British Color Council in collaboration with the Royal Horticultural Society.

In the drawings accompanying this application, the different portions of the leaves, petals and surfaces of the petals of the open rose and bud are indicated as to their color by direct reference to the color charts of this publication. Thus in the bud it is indicated that the tip of the bud has a straw yellow color comparable with the color chart 604/1 and 604/2. The darkest portion of the bud petal has a color of Plate 619/1 of the shading of the Begonia plates, shading to the lighter Begonia Pinks of Plates 619/2 and 619/3. The base of the petals has the color comparable with color Chart 604/1 shading to Chart 604/2, or a straw yellow color.

The petals of the open flower are colored at their darkest portion of Shrimp Red comparable with Chart 616 and shading through the shades of Shrimp Red as indicated by the color Charts 616/1, 616/2 and 616/3.

In the full bloom rose the color shadings are comparable with those of the rose in partial full bloom, the petals being of the shades of Shrimp Red shading from colors comparable with the Shrimp Red Chart 616, through the colors 616/1, 616/2 and 616/3 as indicated upon the full bloom rose flower.

In the full bloom rose the colors shade to the Chinese Coral of the color Chart 614/3 to the yellows of Carrot Red comparable with color Chart 612.

The center of the rose has the color of Straw Yellow of Chart 604/1 and the deep yellows of the stamen is Chinese Yellow comparable with the color Chart 606.

The color of the leaves of the rose plant are not materially different from that of the parent rose "Picture," being of the Willow Green shading from Plate 000862 to the lighter shade of Plate 000862/1 as indicated.

I claim:

The variety of rose plant herein disclosed, characterized by the shadings of the petals of the buds and open rose flowers which are respectively Begonia Pink and Shrimp Red shades, shading to Straw Yellow at their base and tips, and further characterized by the fact that the flowers have fewer petals than the parent "Picture" rose.

LESLIE A. TUTTLE.

No references cited.